(12) United States Patent
Walker et al.

(10) Patent No.: US 6,548,546 B2
(45) Date of Patent: Apr. 15, 2003

(54) HIV INTEGRASE INHIBITORS

(75) Inventors: Michael A. Walker, Durham, CT (US); Timothy D. Johnson, Durham, NC (US); Oak K. Kim, Cambridge, MA (US); Yunhui Zhang, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 34 days.

(21) Appl. No.: 10/085,314

(22) Filed: Feb. 28, 2002

(65) Prior Publication Data

US 2002/0123527 A1 Sep. 5, 2002

Related U.S. Application Data

(63) Continuation of application No. 09/884,731, filed on Jun. 18, 2001, now abandoned.
(60) Provisional application No. 60/211,900, filed on Jun. 16, 2000.

(51) Int. Cl.$^7$ ............... A61K 31/19; C07C 62/38; C07C 65/34; C07C 59/90
(52) U.S. Cl. .............. 514/569; 514/568; 514/570; 562/459; 562/461; 562/462; 562/463
(58) Field of Search ............... 562/459, 461, 562/463, 462; 514/568, 569, 570

(56) References Cited

U.S. PATENT DOCUMENTS 6,306,891 B1 * 10/2001 Selnick et al.

OTHER PUBLICATIONS

Hazuda et al , Inhibitors of Strand Transfer That Prevent Integration and Inhibit HIV–1 Replication in Cells, Jan. 28, 2000, Science, vol. 287 (5453), pp. 646–650.*

Thomassini et al, Inhibition of Cap (m7GpppXm)–Dependent Endonuclease of Influenza Virus by 4–Substituted 2,4–Dioxobutanoic Acid Compounds, 1994, Antimicrobial Agents and Chemotherapy, 38(12) pp. 2827–2837.*

Mournier et al 1997, Pyruvate–extended Amino Acid Derivatives as Highly Potent Inhibitors of Carboxyl–terminal Peptide Amidation, The Journal of Biological Chemistry, 272(8), pp. 5016–5023.*

Charles C.J. Carpenter, et al., "Antiretroviral Therapy in Adults", JAMA 2000, vol. 283, No. 3, p. 381–391 (Jan. 19, 2000).

Nouri Nemati, et al., "Design and Discovery of HIV–1 Integrase Inhibitors", Drug Disc. Today, vol. 2, No. 11, p. 487–498 (Nov. 1997).

Frank J. Palella, et al., "Declining Morbidity and Mortality among Patients with Advanced Human Immunodeficiency Virus Infection", New Engl. J. Med., vol. 338, No. 13, p. 853–860 (Mar. 26, 1998).

* cited by examiner

Primary Examiner—Johann Richter
Assistant Examiner—Paul A. Zucker
(74) Attorney, Agent, or Firm—David M. Morse

(57) ABSTRACT

The present invention relates to HIV integrase inhibitors of the formula

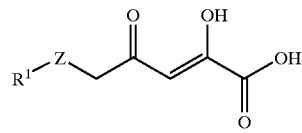

wherein R$^1$ and Z are as defined in the specification.

13 Claims, No Drawings

HIV INTEGRASE INHIBITORS

RELATED APPLICATIONS

This non-provisional application is a continuation of 09/884,731 filed Jun. 18, 2001, now abandoned, which claims the benefit of U.S. Provisional Application No. 60/211,900 filed Jun. 16, 2000.

BACKGROUND

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavaridine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C. J.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S. G.; Richman, D. D.; Saag, M. S.; Schecter, M.; Schoolery, R. T.; Thompson, M. A.; Vella, S.; Yeni, P. G.; Volberding, P. A. *JAMA* 2000, 283, 381). Clearly there is a need for new antiviral agents, preferably targeting other viral enzymes to reduce the rate of resistance and suppress viral replication even further.

HIV expresses three enzymes, reverse transcriptase, an apartyl protease and integrase, all of which are potential antiviral targets for the development of drugs for the treatment of AIDS. However, integrase stands out as being the only viral enzyme not targeted by current therapy. The integrase enzyme is responsible for insertion of the viral cDNA into the host cell genome, which is a critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious. Therefore, an inhibitor of integrase would be useful as a therapy for AIDS and HIV infection.

A number of inhibitors of the enzyme have been reported. These include, nucleotide-based inhibitors, known DNA binders, catechols and hydrazide containing derivatives (Nemati, N.; Sundar, S.; Pommier, Y., *Drug Disc. Today,* 1997, 2, 487). However, no clinically active compound has resulted from these leads.

Thus, what is needed is a clinically effective inhibitor of the HIV integrase enzyme.

SUMMARY OF THE INVENTION

The present invention relates to compounds of Formula I, or a tautomer of said compound, or a pharmaceutically acceptable salt, solvate or prodrug of a compound of Structural Formula I or of a tautomer thereof.

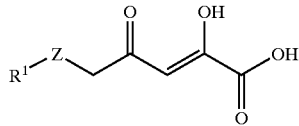

Formula I

In Formula I, $R^1$ is phenyl, wherein said phenyl is substituted from 1–3 times with $R^2$, or $R^1$ naphthyl, wherein said naphthyl is optionally substituted from 1–3 times with R2; each $R^2$ is independently selected from halo, $C_1$–$C_3$ alkyl, $C_1$–$C_2$ alkoxy, $C_1$–$C_3$ haloalkyl, and phenyl-$(CH_2)_mO_n$—; m is 0 or 1; n is 0 or 1; and Z is methylene or —C(O)—, provided that when Z is methylene said substituted phenyl is not para-methoxy phenyl or when Z is —C(O)— said substituted phenyl is not ortho-chloro phenyl.

The present invention also relates to a method of inhibiting HIV integrase by administering to a patient an effective amount of a compound of Structural Formula II, or a tautomer of said compound, or a pharmaceutically acceptable salt, solvate or prodrug of a compound of Structural Formula II or of a tautomer thereof.

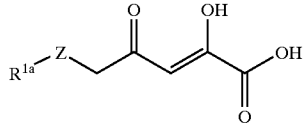

Formula II

In Formula II, Z and $R^2$ are as defined for Formula I, whereas $R^{1a}$ is phenyl or naphthyl, wherein $R^{1a}$ is optionally substituted from 1–3 times with $R^2$, provided that when Z is —C(O)— said substituted phenyl is not ortho-chloro phenyl.

The present invention further relates to a method of treating a patients infected by the HIV virus, or of treating AIDS or ARC, by administering to the patient an effective amount of a compound of Structural Formula II, or a tautomer of said compound, or a pharmaceutically acceptable salt, solvate or prodrug of a compound of Structural Formula II or of a tautomer thereof.

Another embodiment includes a pharmaceutical composition, useful for inhibiting HIV integrase, or for treating patients infected with the HIV virus, or suffering from AIDS or ARC, which comprises a therapeutically effective amount of one or more of the compounds of Formula II, including a tautomer of said compound, or a pharmaceutically acceptable salt, solvate or prodrug of a compound of Structural Formula II or of a tautomer thereof, and a pharmaceutically acceptable carrier.

DETAILED DESCRIPTION OF THE INVENTION

In the present invention, unless otherwise specified the following definitions apply.

The numbers in the subscript after the symbol "C" define the number of carbon atoms a particular group can contain. For example, "$C_1$–$C_6$" means a substituent containing from one to six carbon atoms.

As used herein, the term "alkyl" means a saturated, straight chain or branched monovalent hydrocarbon radical having the stated number of carbon atoms. Examples of such alkyl radicals include methyl, ethyl, n-propyl and isopropyl.

Haloalkyl refers to an alkyl radical that is substituted with one or more halo radicals, such as trifluoromethyl.

The term "alkoxy" means any of methoxy, ethoxy, n-propoxy, isopropoxy and the like.

"Halo" means chloro, bromo, iodo or fluoro radicals.

By virtue of its acidic moiety, where applicable, a compound of Formula I forms salts by the addition of a pharmaceutically acceptable base. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino aids such as lysine, arginine and N-methylglutamine. These salts may be prepared by methods known to those to skilled in the art.

Certain compounds of Formula I, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

This invention also encompasses pharmaceutically acceptable prodrugs of the compounds of Formula I. Prodrugs are derivatives of the compounds of the invention which have chemically or metabolically cleavable groups and become, by solvolysis or under physiological conditions, the compounds of the invention which are pharmaceutically active in vivo.

A prodrug of a compound of Structural Formula I may be formed in a conventional manner with a functional group of the compounds such as with an amino, hydroxy or carboxy group. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or (alkoxycarbonyl)oxy)alkyl esters. Examples of prodrugs of compounds of the present invention include the compounds described in Examples 143–146 as well as the ester chemical intermediates from which the compounds of Examples 1–57 were formed.

Certain compounds of Structural Formula I may also exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

The compounds of this invention, as they are keto-acid, can also exist as tautomers. Therefore the present invention also includes all tautomeric forms.

The compounds of Formula II are useful in the inhibition of HIV integrase, the prevention or treatment of infection by the human immunodeficiency virus and the treatment of consequent pathological conditions such as AIDS or ARC. The treatment involves administering to a patient, in need of such treatment, a compound of Formula II, or a tautomer of said compound, or a pharmaceutically acceptable salt, solvate or prodrug of a compound of Structural Formula II or of a tautomer thereof, or a pharmaceutical composition comprising a pharmaceutical carrier and a therapeutically effective amount of a compound of the present invention, or a tautomer of said compound, or a pharmaceutically acceptable salt, solvate or prodrug of a compound of Structural Formula II or of a tautomer thereof.

It will be appreciated by those skilled in the art that reference herein to treatment extends to prophylaxis as well as the treatment of established infections or symptoms. This includes initiating treatment pre- and post-exposure to the virus. In addition, the present invention can be administered in conjunction with other anti-HIV agents, immunomodulators, antiinfectives and/or vaccines.

The compounds of the present invention are also useful in the preparation and execution of screening assays for antiviral compounds. Further, the compounds of the present invention are useful in establishing or determining the binding site of other antiviral compounds to HIV integrase, for example, by competitive inhibition.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

This invention also provides a pharmaceutical composition for use in the above-described therapeutic method. A pharmaceutical composition of the present invention comprises an effective amount of a compound of Formula I in association with a pharmaceutically acceptable carrier, excipient or diluent.

The active ingredient in such formulations comprises from 0.1 percent to 99.9 percent by weight of the formulation. By "pharmaceutically acceptable' it is meant that the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like.

The compounds can be administered by a variety of routes including oral, intranasally, rectal, transdermal, subcutaneous, intravenous, intramuscular and intranasal.

When administered orally, these compositions are prepared according to techniques well-known in the art of pharmaceutical formulation. For oral administration, the compound is typically formulated with excipients such as binders, fillers, lubricants, extenders, diluents, disintegration agents and the like as are known in the art.

For parenteral administration, the compound is formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

A compound of the present invention, or a salt or solvate thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds of the present invention can also be administered to humans in a dosage range of 1 to 100 mg/kg body weight in divided doses. One preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the route of administration, the age, body weight, general health, sex, diet, mode and time of administration, rate of excretion, drug combination, the severity of the particular condition, and the host undergoing therapy.

General methods useful for the synthesis of compounds embodied in this invention are shown below. The preparations shown below are disclosed for the purpose of illustration and are not meant to be interpreted as limiting the processes to make the compounds by any other methods.

It will be appreciated by those skilled in the art that a number of methods are available for the preparation of the compounds of the present invention as provided by Structural Formula I. A compound of Structural Formula I may be prepared by processes which include processes known in the chemical art for the production of structurally analogous compounds or by a novel process described herein. A process for the preparation of a compound of Structural Formula I (or a pharmaceutically acceptable salt thereof) and novel intermediates for the manufacture of a compound of Formula I, as defined above, provide further features of the invention and are illustrated by the following procedures in which the meanings of the generic radicals are as defined above, unless otherwise specified. It will be recognized that it may be preferred or necessary to prepare a compound of Formula I in which a functional group is protected using a conventional protecting group then to remove the protecting group to provide the compound of Formula I.

Thus, there is provided a process for preparing a compound of Formula I (or a pharmaceutically acceptable salt thereof) as provided in any of the above descriptions which is selected from any of those described in the examples, including the following.

Compounds of the present invention, such as those shown in Examples 1–3, were prepared as illustrated in the following Scheme I.

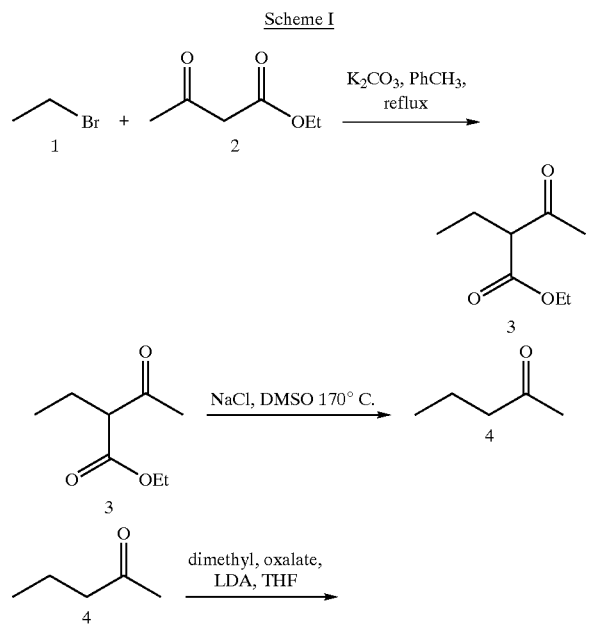

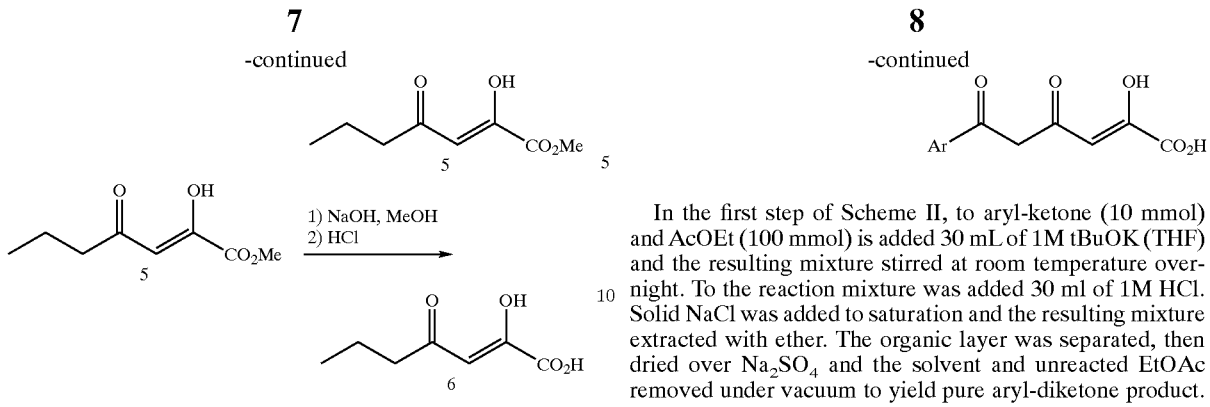

In the first step of Scheme I aryl-methylbromide (1) is reacted with ethyl acetoacetate (2) under basic conditions to yield (3). Well-known variations of this method exist involving the use alternative bases and leaving groups other than bromine. Decarboxylation can be carried out by heating the ethyl ester in DMSO to yield (4) (Fehr, C.; Galindo, J.; Haubrichs, R.; Perret, R. Helv. Chim. Acta. 1989, 72, 1537). It will be appreciated by those skilled in the art that decarboxylation of β-keto esters can be carried out by a number of different methods. For example, this transformation can be also be accomplished by saponification of the ester with NaOH followed by spontaneous loss of $CO_2$ from the intermediate acid. In other variations the ester is saponified with NaOH then warmed in acid to effect the loss of $CO_2$ from the intermediate β-keto acid or simply treated with $H_2SO_4$ alone. It will further be appreciated that a number of methods for preparing methyl ketones such as (4) starting from a variety of starting materials are well known in the art (Advanced Organic Chemistry, Part B: Reactions and Synthesis, Carey, F. A., Sunberg, R. J., Plenum Press, 1990 New York). For example, an appropriately functionalized t-butyl-ester ($CH_3CO_2tBu$) can be alkylated and the resulting product converted (4) using known methods for converting esters to their corresponding methyl ketone.

The preparation of compounds of the type having Formula I has been described previously (Stiles, M.; Selegue, J. P. J. Org. Chem. 1991, 56, 4067.) and is very similar to that used in the current invention. Compounds of the present invention, as shown in Examples 4–13 were prepared according to the method illustrated in the following Scheme II.

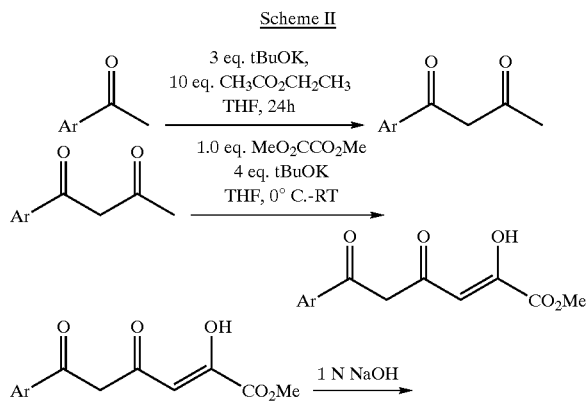

Scheme II

In the first step of Scheme II, to aryl-ketone (10 mmol) and AcOEt (100 mmol) is added 30 mL of 1M tBuOK (THF) and the resulting mixture stirred at room temperature overnight. To the reaction mixture was added 30 ml of 1M HCl. Solid NaCl was added to saturation and the resulting mixture extracted with ether. The organic layer was separated, then dried over $Na_2SO_4$ and the solvent and unreacted EtOAc removed under vacuum to yield pure aryl-diketone product.

In the second step of Scheme II, to aryl-diketone 4.4 mmol) and dimethyl oxalate (4.4 mmol) dissolved in 5 ml of THF at 0° C. is added 17.5 ml of 1M tBuOK (THF) in a rapid stream. The resulting mixture was stirred for 1 h at 0° C. then allowed to regain room temperature and stirred overnight. The reaction was then quenched with 1N HCl. Solid NaCl was added to saturation and the resulting mixture extracted with ether. The organic layer was separated, then dried over $Na_2SO_4$ and the solvent removed under vacuum to yield crude as a yellow solid. The crude product is triturated with hexanes to yield pure ester.

The ester (1.0 mmol) was suspended in 4.0 ml of 1N NaOH and placed in a sonicating bath to dissolve the solid. After 30 min. the resulting solution is washed with $CH_2Cl_2$ then acidified with 1N HCl. The resulting mixture was extracted with $CH_2Cl_2$. The organic layer was dried over $Na_2SO_4$ then the solvent removed to yield pure acid product.

Exemplification

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents.

The abbreviations used herein are conventional abbreviations widely employed in the art. Some of which are: calcd (calculated); DMSO (dimethylsulfoxide); EtOAc (ethyl acetate); HPLC (high-pressure liquid chromatography); LC/MS (liquid chromatography, mass spectroscopy); LDA (lithium diisopropyl amide); LiHMDS (lithium bis (trimethylsilyl)amide); $SiO_2$ (silica gel); THF (tetrahydrofuran), Me (methyl), Et (ethyl), Ph (phenyl), tBuOK (potassium tert-butoxide), NaOMe (sodium methoxide), and NaOEt (sodium ethoxide).

Spectrometry (MS) data were determined with a Micromass ZMD Platform for LC in electrospray mode.

The compounds, used in the method of the present invention, were prepared according to the following methods.

EXAMPLE 1

Intermediate 1A: 4-(2-chloro-phenyl)-butan-2-one

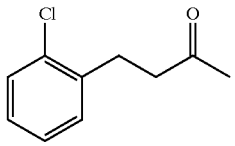

2-Chlorobenzyl bromide (1.28 g, 6.23 mmol), ethyl acetoacetate (810 mg, 6.23 mmol) and $K_2CO_3$ (2.58 g, 18.7 mmol) were combined in 5 ml of toluene and heated to reflux. After 6 h the reaction mixture was cooled to room temperature, stirred an additional 72 h then 100 ml of $H_2O$ and 100 ml of EtOAc added. The organic layer was separated, washed with brine dried over $Na_2SO_4$ then filtered and the solvent removed to yield 1.51 g oil. The oil was taken up in a solution of 1 ml of DMSO and 200 ml of $H_2O$ and NaCl (109 mg, 1.9 mmol) added. The resulting solution was heated to 170° C. for 3 h then cooled to room temperature. 100 ml of petroleum ether was added. The organic layer was separated, washed with brine, dried over $Na_2SO_4$ then filtered and the solvent removed to yield 1.6 g oil. The crude product was purified by column chromatography (7.7×7.5 cm $SiO_2$, 10% EtOAc/Hexanes) to yield 820 mg (72% yield) oil. $^1$H NMR (500 MHz, $CDCl_3$) δ: 2.16 (s, 3), 2.77 (t, 2, J=7), 3.00 (t, 2, J=7), 7.14–7.35 (overlapping m, 4).

Intermediate 1B: 6-(2-chloro-phenyl)-2-hydroxy-4-oxo-hex-2-enoic Acid Methyl Ester

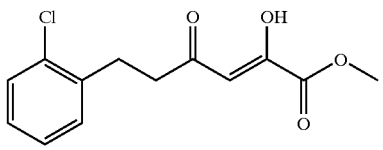

2.7 ml of 2M LDA (Hexane/THF/Ethylbenzene) was diluted in 1.5 ml of $Et_2O$ and cooled to −78° C. To this was added Intermediate 1A (820 mg, 4.5 mmol) dissolved in 4 ml of $Et_2O$. After stirring for 40 min. dimethyl oxalate (584 mg, 4.9 mmol) dissolved in 6 ml of $Et_2O$ was added all at once. The reaction mixture was allowed to warm to room temperature and stirred for 2 h resulting in precipitation of the product as a solid which was isolated by filtration. The solid was added to 1N HCl then extracted with EtOAc. The organic layer was washed with brine, dried over $Na_2SO_4$ then filtered and the solvent removed to yield 830 mg solid. The crude product was purified by column chromatography (4.5×14.5 cm $SiO_2$, 0–3% $EtOH/CH_2Cl_2$) to yield 380 mg (31% yield) solid. MS (M+H) calcd for $C_{13}H_{14}NO_4Cl$: 269.06; found: 269.2. MS (M−H) calcd for $C_{13}H_{12}NO_4Cl$: 267.04; found: 266.92. $^1$H NMR (500 MHz, $CDCl_3$) δ: 2.85 (t, 2, J=7), 3.09 (t, 2, J=7), 3.90 (s, 3), 6.38 (s, 1), 7.16–7.37 (overlapping m, 4). $^{13}$C NMR (125 MHz, $CDCl_3$) δ: 28.58, 40.67, 53.19, 102.04, 127.04, 128.04, 129.69, 130.53, 133.91, 137.69, 102.52, 165.64, 202.05.

Compound 1: 6-(2-chloro-phenyl)-2-hydroxy-4-oxo-hex-2-enoic Acid

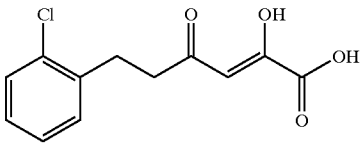

Intermediate 1B (320 mg, 1.2 mmol) was treated with 1.31 ml of 1 N NaOH, a small amount of MeOH was added to aid dissolution of the ester. The resulting suspension was stirred for 2 h then acidified with 1N HCl and EtOAc was added. The organic layer was separated, washed with brine, dried over $Na_2SO_4$ then filtered and the solvent removed to yield 240 mg oil. The crude product was purified by reverse phase preparative HPLC ($C_{18}$, $MeOH/H_2O$ (0.1% TFA)-gradient). MS (M−H) calcd for $C_{12}H_{10}NO_4Cl$: 253.0268; found: 253.0267.

EXAMPLE 2

Intermediate 2A: 2-(2-bromo-benzyl)-3-oxo-butyric Acid Ethyl Ester

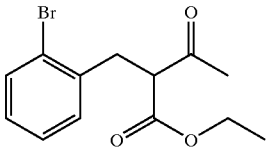

2-Bromobenzyl bromide (1.95 g, 7.8 mmol), ethyl acetoacetate (1.01 g, 7.8 mmol) and $K_2CO_3$ (3.23 g, 23.4 mmol) were combined in 5 ml of toluene and heated to reflux. After 6 h the reaction mixture was cooled to room temperature, stirred an additional 72 h then 100 ml of $H_2O$ and 100 ml of EtOAc added. The organic layer was separated, washed with brine dried over $Na_2SO_4$ then filtered and the solvent removed to yield 2.31 g oil. The crude product was purified by column chromatography (8 cm×10 cm $SiO_2$, 10% EtOAc/Hexanes) to isolate 1.90 g (81% yield) oil. LC/MS (M+H) calcd for $C_{13}H_{16}O_3Br$: 229.03; found: 299.03. $^1$H NMR (500 MHz, $CDCl_3$) δ: 1.21 (t, 3, J=7), 2.24 (s, 3), 3.28 (m, 2), 3.97 (dd, 1, J=7, 8), 4.14 (m, 2), 7.07–7.54 (overlapping m, 4).

Intermediate 2B: 4-(2-bromo-phenyl)-but-2-one

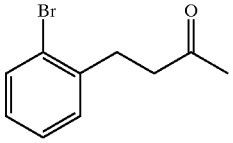

Intermediate 2A (1.90 g, 6.3 mmol) was dissolved in 12 ml of EtOH and treated with 12 ml of 1 N NaOH. The resulting mixture was stirred overnight then acidified to pH 3 with 1 N HCl. EtOAc was added, the organic layer separated, washed with brine then dried over $Na_2SO_4$ and the solvent removed to yield 1.43 g oil. The crude product was purified by column chromatography (5 cm×11.5 cm $SiO_2$, 5% EtOAc/Hexanes) to yield 1.00 g (57% yield) oil. MS (M−H) calcd for $C_{10}H_{10}OBr$: 224.99; found: 224.88. $^1$H NMR (500 MHz, $CDCl_3$) δ: 2.16 (s, 3), 2.77 (t, 2, J=7), 3.00 (t, 2, J=7), 7.05–7.53 (overlapping m, 4). $^{13}$C NMR (125 MHz, $CDCl_3$) δ: 30.01, 30.31, 124.30, 127.62, 127.97, 130.64, 132.89, 140.30, 207.59.

Intermediate 2C: 6-(2-Bromo-phenyl)-2-hydroxy-4-oxo-hex-2-enoic Acid Methyl Ester

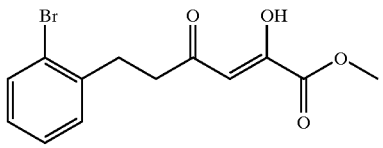

The procedure of Example 1 was used to prepare the methyl ester from Intermediate 2B. LC/MS (M+H) calcd for $C_{13}H_{14}O_4Br$: 313.01; found: 313.01. MS (M−H) calcd for $C_{13}H_{12}O_4Br$: 310.99; found: 310.90. $^1H$ NMR (500 MHz, $CDCl_3$) δ: 2.84 (t, 2, J=7), 3.09 (t, 2, J=7), 3.90 (s, 3), 6.38 (s, 1), 7.08–7.55 (overlapping m, 4). $^{13}C$ NMR (125 MHz, $CDCl_3$) δ: 31.07, 40.84, 53.20, 102.06, 124.31, 127.71, 128.28, 130.53, 133. 02, 139.39, 162.52, 166.00, 202.00.

Compound 2: 6-(2-Bromo-phenyl)-2-hydroxy-4-oxo-hex-2-enoic Acid

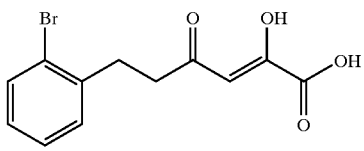

The procedure of Example 1 was used to prepare the Compound 2 from Intermediate 2C. MS (M−H) calcd for $C_{12}H_{10}O_4Br$: 296.97; found: 296.90. HRMS (M−H) calcd for $C_{12}H_{10}O_4Br$: 296.9762; found: 296.9760. $^1H$ NMR (500 MHz, $CDCl_3$) δ: 2.86 (t, 2, J=7), 3.10 (t, 2, J=7), 6.47 (s, 1), 7.04–7.55 (overlapping m, 4). $^{13}C$ NMR (125 MHz, $CDCl_3$) δ: 31.32, 40.07, 101.24, 124.30, 127.69, 128.40, 130.51, 132.94, 139.12, 164.01, 167.70, 200.34.

EXAMPLE 3

Intermediate 3A: 2-Hydroxy-4-oxo-6-phenyl-hex-2-enoic Acid Methyl Ester

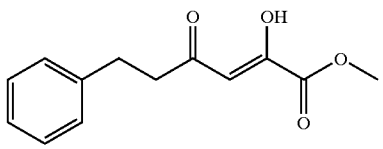

The procedure of Example 1 was used to prepare the methyl ester from 4-phenyl-butan-2-one. LCMS (M+H) calcd for $C_{13}H_{15}O_4$: 235.10; found: 235.06. MS (M−H) calcd for $C_{13}H_{13}O_4$: 233.08; found: 233.01. $^1H$ NMR (300 MHz, deuterated DMSO) δ: 2.44 (t, 2, J=7), 2.79 (t, 2, J=7), 3.63 (s, 3), 5.7 (s, 1), 7.12–7.27 (overlapping m, 5). $^{13}C$ NMR (75 MHz, DMSO) δ: 31.38, 42.91, 51.41, 96.11, 125.62, 128.19, 142.01, 167.26, 169.92, 194.67.

Compound 3: 2-Hydroxy-4-oxo-phenyl-hex-2-enoic Acid

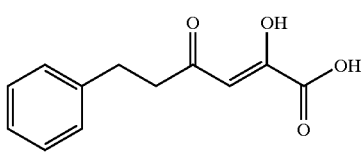

The procedure of Example 1 was used to prepare the hexenoic acid from Intermediate 3A. MS (M+H) calcd for $C_{12}H_{11}O_4$: 219.07; found: 218.97. HRMS (M−H) calcd for $C_{12}H_{11}O_4$: 219.0657; found: 219.0658. $^1H$ NMR (500 MHz, deuterated DMSO) δ: 2.90 (m, 4), 6.32 (s, 1), 7.16–7.29 (overlapping m, 5).

EXAMPLE 4

Intermediate 4A: 6-(2-Benzyloxy-phenyl)-2-hydroxy-4,6,-dioxo-hex-2-enoic Acid Methyl Ester

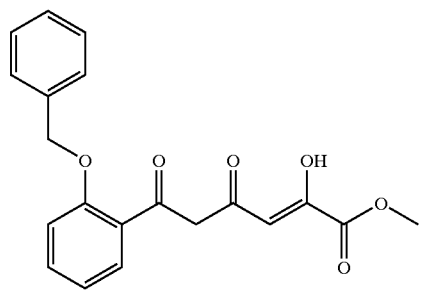

Intermediate 4A was prepared according to the method of Scheme II from 1-(2-benzyloxy-phenyl)-ethanone. MS (M+H) calcd for $C_{20}H_{19}O_6$: 355; found: 355. $^1H$ NMR (500 MHz, acetone-$d_6$), δ: 3.88 (s, 1), 5.35 (s, 2), 6.14 (s, 1), 6.83 (s, 1), 7.11–7.98 (overlapping m, 9).

Compound 4: 6-(2-Benzyloxy-phenyl)-2-hydroxy-4,6,-dioxo-hex-2-enoic Acid

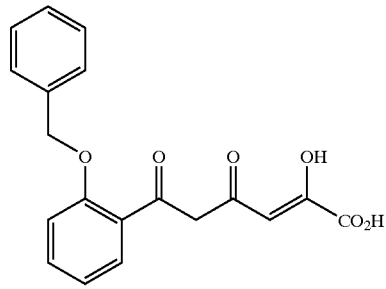

The procedure of Scheme II was used to prepare the Compound 4 from Intermediate 4A. MS (M−H) calcd for $C_{19}H_{15}O_6$: 339; found: 339. $^1H$ NMR (500 MHz, acetone-$d_6$), δ: 5.36 (s, 2), 6.19 (s, 1), 6.84 (s, 1), 7.11–7.98 (overlapping m, 9).

EXAMPLE 5

Intermediate 5A: 2-Hydroxy-4,6-dioxo-6-(2-trifluoromethyl-phenyl)-hex-2-enoic Acid Methyl Ester

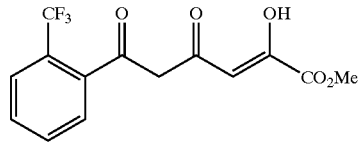

Intermediate 5A was prepared according to the method of Scheme II from 1-_2-trifluoromethyl-phenyl)-ethanone. MS (M+) calcd for $C_{14}H_{11}F_3O_5$: 316; found: 316. $^1H$ NMR (300 MHz, acetone-$d_6$), δ: 3.87 (s, 3), 6.19 (s, 1), 6.38 (s, 1), 7.75–7.92 (overlapping m, 4).

Compound 5: 2-Hydroxy-4,6-dioxo-6-(2-trifluoromethyl-phenyl)-hex-2-enoic Acid

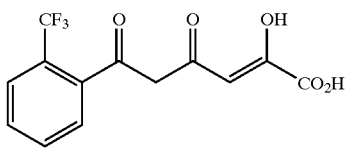

The procedure of Scheme II was used to prepare the Compound 5 from Intermediate 5A. MS (M+H) calcd for $C_{13}H_{10}F_3O_5$: 303; found: 303. $^1$H NMR (300 MHz, acetone-$d_6$), δ: 6.21 (s, 1), 6.40 (s, 1), 7.67–7.98 (overlapping m, 4).

EXAMPLE 6

Intermediate 6A: 2-Hydroxy-6-(2-methoxy-phenyl)-4,6-dioxo-hex-2-enoic Acid Methyl Ester

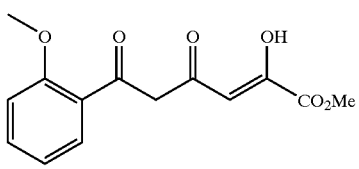

Intermediate 6A was prepared according to the method of Scheme II from 1-(2-methoxy-phenyl)-ethanone. MS (M–H) calcd for $C_{14}H_{13}O_6$: 277; found: 277. $^1$H NMR (300 MHz, acetone-$d_6$) δ: 3.88 (s, 3), 4.00 (s, 3), 6.38 (s, 1), 6.83 (s, 1), 7.07–7.98 (overlapping m, 4).

Compound 6: 2-Hydroxy-6-(2-methoxy-phenyl)-4,6-dioxo-hex-2-enoic Acid

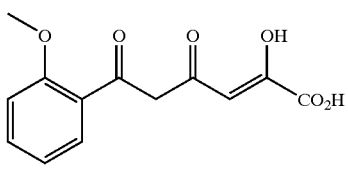

The procedure of Scheme II was used to prepare the Compound 6 from Intermediate 6A. MS (M–H) calcd for $C_{13}H_{11}O_6$: 263; found: 263. $^1$H NMR (300 MHz, acetone-$d_6$) δ: 4.01 (s, 3), 6.41 (s, 1), 6.83 (s, 1), 7.09–7.98 (overlapping m, 4).

EXAMPLE 7

Compound 7: 2-Hydroxy-6-naphthalen-2-yl-4,6-dioxo-hex-2-enoic Acid

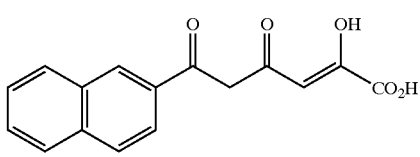

The procedure of Scheme II was used to prepare the Compound 7 from 1-naphthalen-2-yl-ethanone. MS (M$^+$) calcd for $C_{16}H_{12}O_5$: 284; found: 284. $^1$H NMR (300 MHz, acetone-$d_6$) δ: 6.51 (s, 1), 6.80 (s, 1), 7.62–8.66 (overlapping m, 7).

EXAMPLE 8

Intermediate 8A: 6-(2,4,-Dichloro-phenyl)-2-hydroxy-4,6-dioxo-hex-2-enoic Acid Methyl Ester

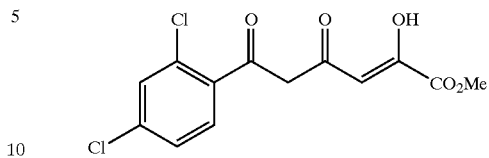

Intermediate 8A was prepared according to the method of Scheme II from 1-(2,4-dichloro-phenyl)-ethanone. MS (M–H) calcd for $C_{13}H_9Cl_2O_5$: 315; found: 315. $^1$H NMR (300 MHz, CDCl$_3$) δ: 3.93 (s, 3), 6.10 (s, 1), 6.32 (s, 1), 7.35–7.66 (overlapping m, 3), 13.2 (s, 1), 14.9 (s, 1).

Compound 8: 6-(2,4,-Dichloro-phenyl)-2-hydroxy-4,6-dioxo-hex-2-enoic Acid

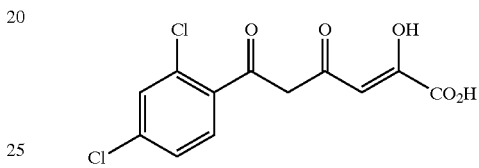

The procedure of Scheme II was used to prepare the Compound 8 from Intermediate 8A. MS (M+H) calcd for $C_{12}H_9Cl_2O_5$: 303; found: 303. $^1$H NMR (300 MHz, acetone-$d_6$) δ: 6.39 (s, 1), 6.43 (s, 1), 7.55–7.79 (overlapping m, 3).

EXAMPLE 9

Intermediate 9A: 6-Biphenyl-4-yl-2-hydroxy-4,6-dioxo-hex-2-enoic Acid Methyl Ester

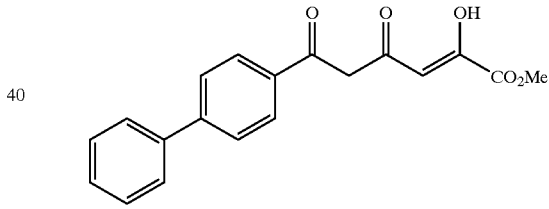

Intermediate 9A was prepared according to the method of Scheme II from 1-bi-phenyl-4-yl-ethanone. MS (M$^+$) calcd for $C_{19}H_{16}O_5$: 324; found: 324. $^1$H NMR (300 MHz, CDCl$_3$) δ: 3.94 (s, 1), 6.18 (s, 1), 6.36 (s, 1), 7.40–7.98 (overlapping m, 9), 13.32 (s, 1), 15.14 (s, 1).

Compound 9: 6-Biphenyl-4-yl-2-hydroxy-4,6-dioxo-hex-2-enoic Acid

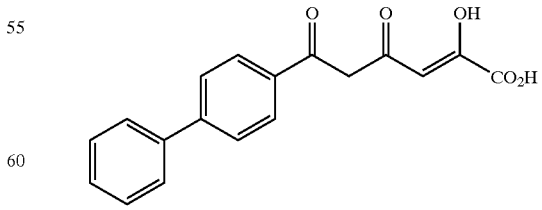

The procedure of Scheme II was used to prepare the Compound 9 from Intermediate 9A. MS (M$^+$) calcd for $C_{18}H_{14}O_5$: 310; found: 310. $^1$H NMR (500 MHz, acetone-$d_6$) δ: 6.48 (s, 1), 6.70 (s, 1), 7.42–8.13 (overlapping m, 9).

EXAMPLE 10

Intermediate 10A:(3-Chloro-phenyl)-2-hydroxy-4,6-dioxo-hex-2-enoic Acid Methyl Ester

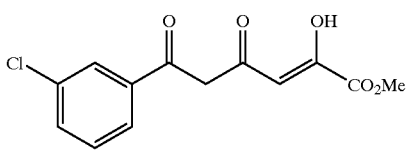

Intermediate 10A was prepared according to the method of Scheme II from 1-(3-chloro-phenyl)-ethanone. MS (M+) calcd for $C_{13}H_{11}ClO_5$: 282; found: 282. $^1$H NMR (300 MHz, CDCl$_3$) δ: 3.94 (s, 3), 6.11 (s, 1), 6.35 (s, 1), 7.40–7.87 (overlapping m, 4), 13.23 (s, 1), 14.98 (s, 1).

Compound 10: 6-(3-Chloro-phenyl)-2-hydroxy-4,6-dioxo-hex-2-enoic Acid

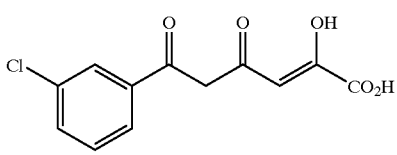

The procedure of Scheme II was used to prepare the Compound 10 from Intermediate 10A. MS (M+) calcd for $C_{12}H_9ClO_5$: 268; found: 268. $^1$H NMR (500 MHz, acetone-d$_6$) δ: 6.48 (s, 1), 6.71 (s, 1), 7.57–8.01 (overlapping m, 4).

EXAMPLE 11

Intermediate 11A: 6-(2-Fluoro-phenyl)-2-hydroxy-4,6,-dioxo-hex-2-enoic Acid Methyl Ester

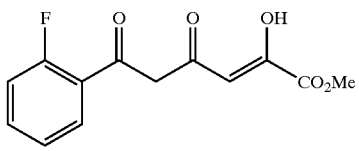

Intermediate 11A was prepared according to the method of Scheme II from 1-(2-fluoro-phenyl)-ethanone. MS (M+) calcd for $C_{13}H_{11}FO_5$: 266; found: 266. $^1$H NMR (300 MHz, CDCl$_3$) δ: 3.93 (s, 3), 6.32 (s, 1), 6.35 (s, 1), 7.14–8.01 (overlapping m, 4), 13.2 (s, 1), 15.1 (s, 1).

Compound 11: 6-(2-Fluoro-phenyl)-2-hydroxy-4,6,-dioxo-hex-2-enoic Acid

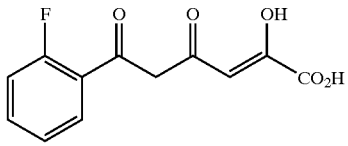

The procedure of Scheme II was used to prepare the Compound 11 from Intermediate 11A. MS (M–H) calcd for $C_{12}H_8FO_5$: 251; found: 251. $^1$H NMR (300 MHz, acetone-d$_6$) δ: 6.47 (s, 1), 6.54 (s, 1), 7.30–8.00 (overlapping m, 4).

EXAMPLE 12

Compound 12: 6-(2,5-Dichloro-phenyl)2-hydroxy-4,6-dioxo-hex-2-enoic Acid

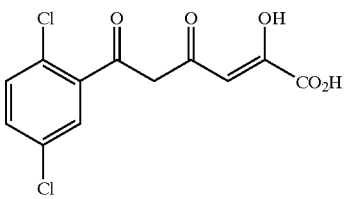

The procedure of Scheme II was used to prepare the Compound 12 from 1-(2,5-dichloro-phenyl)-ethanone. MS (M+) calcd for $C_{12}H_8Cl_2O_5$: 302; found: 302. $^1$H NMR (300 MHz, acetone-d$_6$) δ: 6.40 (s, 1), 6.43 (s, 1), 7.58–7.75 (overlapping m, 3).

EXAMPLE 13

Compound 13: 2-Hydroxy-4,6-dioxo-6-phenyl-hex-2-enoic Acid

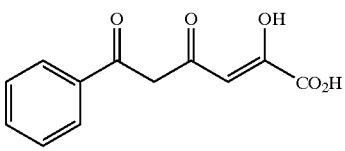

The procedure of Scheme II was used to prepare the Compound 13 from 1-phenyl-ethanone. MS (M–H) calcd for $C_{12}H_9O_5$: 233.05; found: 233.20. $^1$H NMR (300 MHz, CD$_3$CN) δ: 6.40 (s, 1), 6.43 (s, 1), 7.52–8.00 (overlapping m, 5), 15.16 (br s, 1).

Biological Activity

The in vitro activities, against integrase, of compounds of the present invention, were measured in a manner which was similar to previously disclosed methods (cf. Hazuda, D. J.; Felock, P.; Witmer, M.; Wolfe, A.; Stillmock, K.; Grobler, J. A.; Espeseth, A.; Gabryelski, L.; Schleif, W.; Blau, C.; Miller, M. D. Science, 2000, 287, 646) Purified recombinant HIV-1 integrase was incubated with immobilized precleaved substrate DNA in a 96 well plate for 20 min at 37° C. After the integration complex was formed, compounds at desired concentrations were added to the wells followed by a 10 min incubation at 37° C. Biotinyted Target DNA was then added and the reaction was carried out for an additional 1 hour at 37° C. Wells were then washed thoroughly to remove any free DNA and integration activity was measured by using a commercial kit to quantitate the amount of biotinyted target DNA integrated into the substrate.

| Compound Number | % Inhibition of integrase at 70 μM |
|---|---|
| 1 | 70 |
| 2 | 90 |
| 3 | 60 |
| 4 | 97 |
| 5 | 90 |
| 6 | 90 |
| 7 | 95 |
| 8 | 95 |
| 9 | 99 |
| 10 | 88 |

-continued

| Compound Number | % Inhibition of integrase at 70 μM |
|---|---|
| 11 | 86 |
| 12 | 98 |
| 13 | 50 |

We claim:

1. A compound of the formula

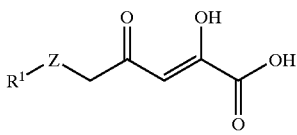

or a tautomer thereof, wherein:
(a) $R^1$ is phenyl, wherein said phenyl is substituted from 1–3 times with $R^2$, or $R^1$ is naphthyl, wherein said naphthyl is optionally substituted from 1–3 times with R2;
(b) each $R^2$ is independently selected from halo, $C_1$–$C_3$ alkyl, $C_1$–$C_2$ alkoxy, $C_1$–$C_3$ haloalkyl, and phenyl-$(CH_2)_mO_n$—;
(c) m is 0 or 1;
(d) n is 0 or 1; and
(e) Z is methylene or —C(O)—, provided that when Z is methylene said substituted phenyl is not para-methoxy phenyl or when Z is —C(O)— said substituted phenyl is not ortho-chloro phenyl,
or a pharmaceutically acceptable salt, solvate or prodrug of said compound or tautomer thereof.

2. A compound of claim 1 wherein Z is methylene.
3. A compound of claim 2 wherein Z is —C(O)—.
4. A pharmaceutical composition, comprising
a) a compound of the formula

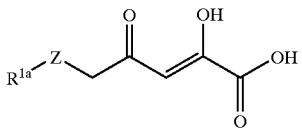

or a tautomer thereof, wherein:
$R^{1a}$ is phenyl, wherein said phenyl is substituted from 1–3 times with $R^2$, or $R^{1a}$ is naphthyl, wherein said naphthyl is optionally substituted from 1–3 times with R2;
each $R^2$ is independently selected from halo, $C_1$–$C_3$ alkyl, $C_1$–$C_2$ alkoxy, $C_1$–$C_3$ haloalkyl, and phenyl-$(CH_2)_mO_n$—;
m is 0 or 1;
n is 0 or 1; and
Z is methylene or —C(O)—, provided that when Z is —C(O)— said substituted phenyl is not ortho-chloro phenyl,
or a pharmaceutically acceptable salt, solvate or prodrug of said compound or tautomer thereof; and
b) a pharmaceutically acceptable carrier.

5. A pharmaceutical composition of claim 4 wherein Z is methylene.
6. A pharmaceutical composition of claim 4 wherein Z is —C(O)—.
7. The pharmaceutical composition of claim 4, further comprising a therapeutically effective amount of one or more other HIV treatment agents selected from
(a) an HIV protease inhibitor,
(b) a nucleoside reverse transcriptase inhibitor,
(c) a non-nucleoside reverse transcriptase inhibitor,
(d) an HIV-entry inhibitor, or
(e) an immunomodulator,
or a combination thereof.

8. A method of inhibiting HIV integrase which comprises administering to a mammal in need of such treatment a therapeutically effective amount a compound of claim 2, of a tautomer thereof, or of a pharmaceutically acceptable salt, solvate or prodrug of said compound or tautomer thereof.
9. A method of inhibiting HIV integrase which comprises administering to a mammal in need of such treatment a therapeutically effective amount a compound of claim 3, of a tautomer thereof, or of a pharmaceutically acceptable salt, solvate or prodrug of said compound or tautomer thereof.
10. A method of treating an HIV infection, in a patient in need thereof, comprising the administration to said patient of a therapeutically effective amount a compound of claim 2, of a tautomer thereof, or of a pharmaceutically acceptable salt, solvate or prodrug of said compound or tautomer thereof.
11. A method of for treating an HIV infection, in a patient in need thereof, comprising the administration to said patient of a therapeutically effective amount a compound of claim 3, of a tautomer thereof, or of a pharmaceutically acceptable salt, solvate or prodrug of said compound or tautomer thereof.
12. A method of therapeutically treating AIDS or ARC, in a patient in need thereof, comprising the administration to said patient of a therapeutically effective amount a compound of claim 2, of a tautomer thereof, or of a pharmaceutically acceptable salt, solvate or prodrug of said compound or tautomer thereof.
13. A method of therapeutically treating AIDS or ARC, in a patient in need thereof, comprising the administration to said patient of a therapeutically effective amount a compound of claim 3; of a tautomer thereof, or of a pharmaceutically acceptable salt, solvate or prodrug of said compound or tautomer thereof.

* * * * *